United States Patent
Lin

(12) 
(10) Patent No.: US 6,213,933 B1
(45) Date of Patent: Apr. 10, 2001

(54) APPARATUS AND METHOD FOR FUNCTIONAL MAGNETIC STIMULATION

(76) Inventor: Vernon Wen-Hau Lin, 12944 Charlwood, Cerritos, CA (US) 90703

( * ) Notice: Subject to any disclaimer, the term of this patent is extended or adjusted under 35 U.S.C. 154(b) by 0 days.

(21) Appl. No.: 09/151,221

(22) Filed: Sep. 10, 1998

(51) Int. Cl.[7] .............................. A61W 1/00; A61W 2/00
(52) U.S. Cl. ................................. 600/13; 600/9
(58) Field of Search ................... 600/9, 10, 11, 600/12, 13, 14, 15; 128/903, 904; 340/573, 666

(56) References Cited

U.S. PATENT DOCUMENTS

| | | | |
|---|---|---|---|
| 936,874 | * 10/1909 | Ellery | 600/13 |
| 4,020,482 | * 4/1977 | Feldl | 340/279 |
| 4,926,866 | * 5/1990 | Lee | 128/630 |
| 4,947,152 | * 8/1990 | Hodges | 340/573 |
| 5,108,359 | * 4/1992 | Granov et al. | 600/9 |
| 5,338,286 | * 8/1994 | Abbott et al. | 600/14 |
| 5,441,495 | * 8/1995 | Liboff et al. | 600/9 |
| 5,496,258 | * 3/1996 | Anninos et al. | 600/13 |
| 5,527,259 | * 6/1996 | Grace et al. | 600/14 |
| 5,593,379 | * 1/1997 | Rayman | 600/9 |
| 5,595,564 | * 1/1997 | Pinna | 600/14 |
| 5,707,334 | * 1/1998 | Young | 600/9 |
| 5,780,798 | * 7/1998 | Hall-Jackson | 200/85 |
| 5,808,552 | * 9/1998 | Wiley et al. | 340/562 |

FOREIGN PATENT DOCUMENTS

WO 91/15263 * 10/1991 (WO) .................................. 600/13

* cited by examiner

Primary Examiner—Samuel G. Gilbert
Assistant Examiner—Joseph A. Cadugan
(74) Attorney, Agent, or Firm—Forrest L. Collins

(57) ABSTRACT

This invention deals with inducing fibrinolysis in a human subject through electro-magnetic induction. The claimed method provides a non-invasive procedure to stimulate fibrinolysis in individuals such as quadriplegic patients, or others needing fibrinolytic stimulation.

18 Claims, 2 Drawing Sheets

APPARATUS AND METHOD FOR FUNCTIONAL MAGNETIC STIMULATION

BACKGROUND OF THE INVENTION

1. Field of the Invention

The purpose of this invention is to employ Functional Magnetic Stimulation by electro-magnetic induction to enhance fibrinolysis.

2. Description of the Art Practices

In most normally functioning human subjects sufficient muscle function exists to minimize the formation of embolisms or thrombosis. However, any individual may develop embolisms or thrombosis due to periods of inactivity. Such inactivity often results from a hospital stay. In individuals with conditions such as paraplegia, quadriplegia or for comatose patients the periods of inactivity are prolonged. For any hospital patient there is a need for stimulation, particularly of the legs to avoid the formation of embolisms or thrombosis.

An article entitled *Effects of External Pneumatic Intermittent Compression on Fibrinolysis in Man* published in The Lancet, pages 1412 et seq., Dec. 22, 1973 by Allenby et al., discusses the needs of surgical patients. In particular, Allenby et al., found that external pneumatic intermittent compression applied to the legs of patients undergoing surgery stimulates fibrinolysis during the postoperative period, when normally fibrinolysis would be expected to be depressed. Allenby et al., determined that intermittent compression applied externally to the calf during surgery and for 48 hours afterwards was a safe and effective method of preventing postoperative venous thrombosis in patients with non-malignant disease.

Richard T. Katz et al., in an article entitled, *Functional Electric Stimulation to Enhance Systemic Fibrinolytic Activity in Spinal Cord Injury Patients* published Arch Phys Med Rehabil Vol 68, July 1987 discusses electrical stimulation of spinal cord injury patients. The Katz, et al., article discusses the functional electric stimulation of muscle has been used to decrease the incidence of postoperative deep vein thrombosis in neurologically intact individuals.

In U.S. Pat. No. 3,658,651 issued Apr. 25, 1972 to Maclean there is discussed a method of treatment by placing a patient or an animal to be treated between the poles of an electro-magnet. The patient or an animal is then subjected to an a pulsating magnetic field induced by an intermittent direct current to the electro-magnet with the peak intensity of each pulse being at least 2,000 gauss. The Maclean patent discusses as potential effects of his treatment the clearing of the stimulation of the endocrine glands, relief of pain, suppression of cough, and pleural effusion, energizing effects, clearing of the sensorium, relaxation of muscle spasm, development of peace of mind, and sense of well being, and increase of libido.

Linder in U.S. Pat. No. 5,190,036 issued Mar. 2, 1993 teaches an abdominal binder comprising an electrode belt for stimulating cough in a quadriplegic patient. Linder further discusses stimulating cough in a quadriplegic patient Chest Volume 103 number Jan. 1, 1993 pages 166–199 article entitled Functional Electrical Stimulation to Enhance Cough in Quadriplegia.

Mouchawar, in an article entitled Closed-Chest Cardiac Stimulation with a Pulsed Magnetic Field, *Medical & Biological Engineering & Computing* March 1992, page 162 discusses magnetic stimulator to generate intense, rapidly changing magnetic fields capable of stimulating nerves. Magnetic resonance systems utilizing coplanar coils to provide a pulsed magnetic field with an average of 12 kilojoules to achieve closed-chest magnetically induced ectopic beats. The Mouchawar article also describes the peak-induced electrical field for threshold stimulation at 213 V/m for a 571 micro-second damped sine wave pulse.

Mouchawar et al., in an article entitled Magnetic Electrophrenic Nerve Stimulation to Produce Inspiration, published in the *Annals of Biomedical Engineering*, Volume 19, 1991 pages 219–221 discusses producing inspiration in a dog. The induced inspiration reported by Mouchawar et al., is plotted by integrating the inspiratory air-flow velocity record.

The author of the present patent published a note in entitled Magnetic Stimulation of the Intercostal Muscles at page 1237 of the Archives of Physical Medicine and Rehabilitation volume 74, November 1993. The present author has contributed to a note entitled the High Frequency Magnetic Stimulation of the Inspiratory Muscles which was published in *Muscle & Nerve* October 1993 Volume 16 number 10 at page 1088.

Manual methods of aiding respiration are discussed in U.S. Pat. No. 4,977,889 issued Dec. 18, 1990 to Budd. In the Budd patent a vest is utilized to stimulate respiration.

In a paper entitled Thoracic Spinal Nerve and Root Conduction: A Magnetic Stimulation Study Magnetic Stimulation of the Thoracic Nerves is discussed by Chokroverty et al. The Chokroverty et al., article was published in *Muscle & Nerve* September 1995 Volume 18, number 10 at pages 987–991.

Percutaneous magnetic stimulation is discussed in an article entitled Ventilatory Effects of Percutaneous Magnetophrenic Stimulation by Nagano et al. The Nagano et al., article was published in the *Frontiers of Medical Biological Engineering*, Volume 3, Number 2, pages 97–112 in 1991. An article entitled Cough in Spinal Cord Injured Patients: Comparison of Three Methods to Produce Cough was published by Jaeger et al., in the *Archives of Physical Medical Rehabilitation* Volume 74, December 1993 at pages 1358–1361. The Jaeger article, discusses various methods of phrenic nerve stimulation. The Jaeger et al., article discloses artificial cough reflex stimulation in U.S. Pat. No. 5,314,454 issued May 24, 1994.

The effect of lung volume on transdiaphrematic pressure is discussed in an article by Hamnegard et al. The Hamnegard et al., article appears in the *European Respiratory Journal* 1995 Volume 8, pages 1532–1536.

Voorhees III et al., in a technical note in the *Journal of Clinical Engineering* September/October 1990 page 407 entitled Magnetically Induced Contraction of the Inspiratory Muscles in Dog discusses short-duration inspirations by discharging a capacitor bank into an excitation coil placed over the lower right chest. The Voorhees III article discusses utilizing the construction of the excitation coil as having 59 turns of ¼ inch copper ribbon 0.0200 inches thick wound on a ¾" diameter plastic rod where the outer diameter of the coil is 3.75" and the entire coil is potted in silicon rubber.

The inductance per Voorhees III et al., is 139 micro-H and the resistance is 0.084 ohms. The current was delivered to the coil from a 100-micro F capacitor bank. The resonant frequency of the system was 1350 Hz and the damping coefficient was 0.05. Cadwell Laboratories, Inc. in Application Notes AP-2 Rev. 1 Feb. 22, 1990, discusses high speed magnetic stimulator characteristics.

In an article entitled Developing a More Focal Magnetic Stimulator Part I: Some Basic Principals by Cohen et al., as recorded in *Journal of Clinical Neurophysiology*, 8 (1); 102–111 (1991) magnetic stimulation is discussed generally. Similar disclosures are made by Yunokuchi et al., in the *Journal of Clinical Neurophysiology*, 8 (1); 112–120 (1991) in an article entitled Developing a More Focal Magnetic Stimulator. Part II: Fabricating Coils and Measuring Induced Current Distributions.

The reader is also referred to *Magnetic Stimulation in Clinical Neurophysiology* edited by Sudhansu Chokroverty and published by Butterworths, Boston, London, Singapore, Sydney, Toronto, and Wellington Chapter 3 pages 17 through 32, pages showing FIGS. 7–18; 14-1; 17-4; 17-10, 18-3 and 18-4.

Further reference is made to Magnetic Brain Stimulation With a Double Coil: The importance of Coil Orientation by Mills et al., published in *Electroencephalography and Clinical Neurophysiology*, 85 (1992) pages 17–21. Reference is also made to a publication entitled the Effects of Coil Design on Delivery of Focal Magnetic Stimulation-Technical Considerations Cohen et al., in *Electroencephalography and Clinical Neurophysiology*, 75 (1990) pages 350–357.

The assessment of nerve and muscle function is discussed in a paper entitled Comparison of Cervical Magnetic Stimulation and Bilateral Percutaneous Electrical Stimulation of the Phrenic Nerves in Normal Subjects as reported in *European Respiratory Journal* 1994 Volume 7, pages 1788–1702.

A summary of the results presented in this patent was submitted for publication as *Functional Magnetic Stimulation—A New Modality for Enhancing Systemic Fibrinolysis* by Lin et al. A summary of related research in cough reflex was submitted for publication entitled, *Functional Magnetic Stimulation of The Expiratory Muscles for Cough* by Lin et al.

To the extent that the foregoing references are relevant to the present invention, they are herein specifically incorporated by reference. Where temperatures are given, they are in degrees C unless otherwise indicated. Pressure measurements are reported in centimeters of water. Percentages and ratios given herein are by weight unless otherwise indicated. Measurements herein are stated in degrees of approximation and where appropriate the word "about" may be inserted before any measurement.

SUMMARY OF THE INVENTION

An apparatus, according to the present invention, for treating a human subject with electro-magnetic induction, said apparatus comprising:

a platform having a length and width, said platform length and width of sufficient dimensions to accommodate an adult human subject, said platform comprising a first surface upon which a human subject, when said apparatus is in use, lies, at least one traversing means connected with said platform, said traversing means having mounted thereon an electromagnetic induction coil, said electro-magnetic induction coil being movable along at least one axis of said traversing means, for when said apparatus is in use, permitting focusing of electro-magnetic induction upon said human subject is described herein.

A method of treating a human subject with an apparatus, said apparatus comprising:

a platform having a length and width, said platform length and width of sufficient dimensions to accommodate an adult human subject, said platform comprising a first surface upon which a human subject, when said apparatus is in use, lies, at least one traversing means connected with said platform, said traversing means having mounted thereon an electromagnetic induction coil, said electro-magnetic induction coil being movable along at least one axis of said traversing means, for when said apparatus is in use, permitting focusing of electro-magnetic induction upon said human subject including the steps of exposing the human subject to sufficient electro-magnetic induction for a sufficient period of time to stimulate endogenous fibrinolysis wherein, more than one electro-magnetic induction is employed per single treatment with an interval between the electro-magnetic inductions from 0.5 to 20 seconds, the electro-magnetic induction is employed in cycles of 0.25 to 20 seconds, and the maximum radiation strength per cycle of the electro-magnetic induction is less than about 50 microcurie per electro-magnetic induction.

The present invention describes a method for treating a human subject, in need of treatment for thrombosis, including the steps of exposing the human subject to sufficient electro-magnetic induction for a sufficient period of time to stimulate endogenous fibrinolysis and thereby reduce the tendency of the subject to the thrombosis.

The present invention further describes a method for treating a human subject, in need of treatment for embolism, including the steps of exposing the human subject to sufficient electro-magnetic induction for a sufficient period of time to stimulate endogenous fibrinolysis and thereby reduce the tendency of the subject to the embolism.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

With more particular reference to the drawings the following is set forth.

DETAILED DESCRIPTION OF THE INVENTION

As previously discussed the invention deals with a non-physically invasive method to stimulate the muscles, particularly the leg muscles, to prevent, diminish the tendency to form, or reduce existing thrombi and/or emboli. The present invention is directed to artificially stimulating in a human subject requiring such fibrinolytic stimulation to prevent, diminish the tendency to form, or reduce existing thrombi and/or emboli.

In the present invention the lysis function is stimulated with a functional electro-magnectic stimulator. The equipment utilized for the functional electro-magnectic stimulation (electro-magnectic induction) of the lysis function is conveniently available as a Dantec MagPro Magnetic Stimulator having a round coil 13.5 centimeters in diameter. A further functional electro-magnectic stimulator useful in the present invention is the Cadwell HS M E S-10 Magnetic Stimulator 12 which is available from Cadwell Laboratories, Inc. 909 N. Kellogg Street, Kennewick, Wash. 99336. In any event, any suitable electro-magnectic stimulation device may be utilized in the present invention.

Figure 1:
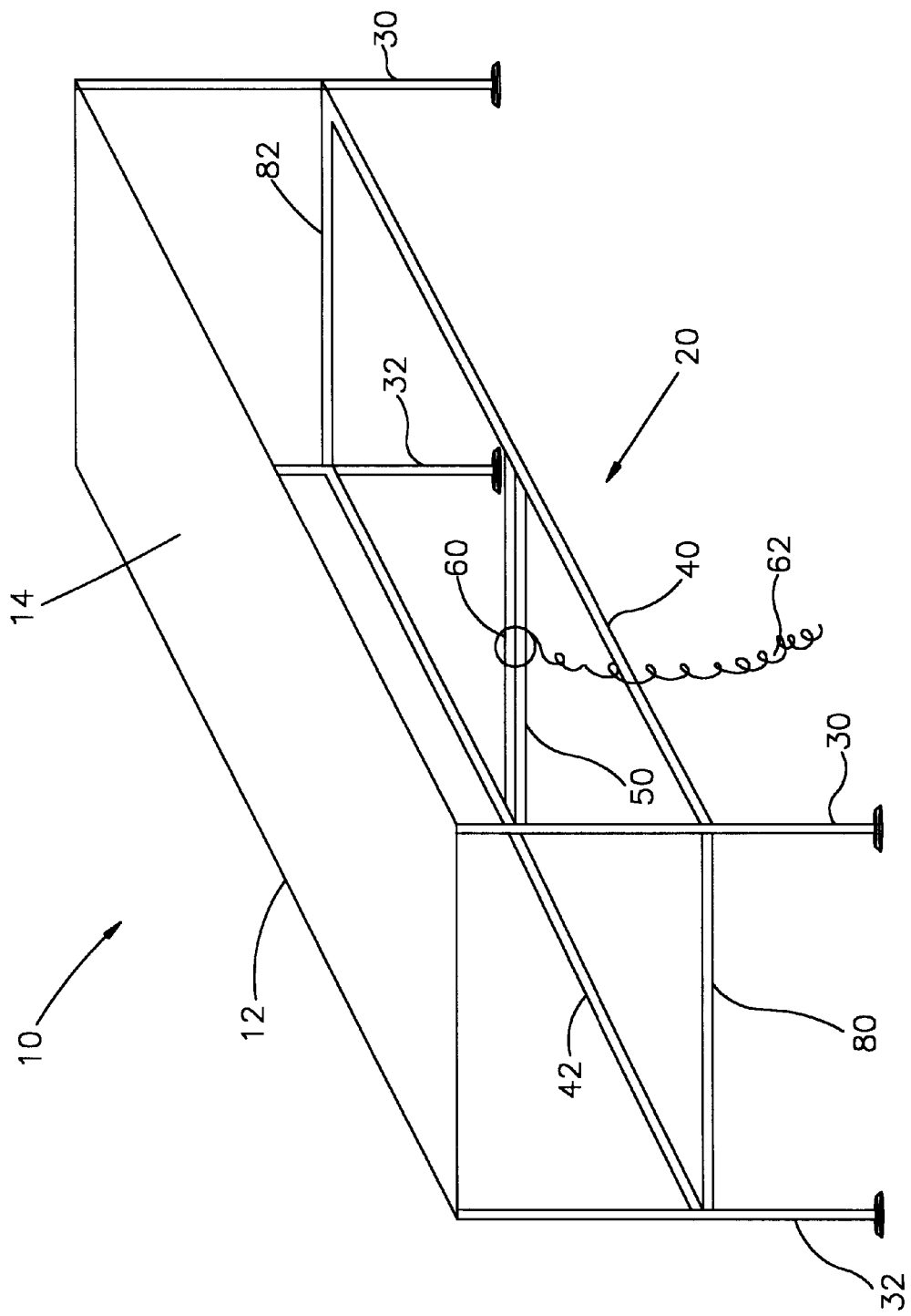
FIG. 1 shows the basic design of an apparatus, according to the present invention, for treating a human subject with electro-magnectic induction.

An apparatus 10 comprises in part a platform 12 (FIG. 1). The platform 12 has an upper flat surface 14. The apparatus also comprises a functional electro-magnectic stimulator 20. The platform 12 is mounted perpendicularly to two legs 30. The platform 12 is also mounted perpendicularly to two legs 32. A first long crossbar 40 is attached to one of each of the two legs 30. A second long crossbar 42 is attached to one of each of the two legs 32. The first long crossbar 40 is generally parallel to the second long crossbar 42. The first long crossbar 40 serves to stabilize the two legs 30 to which the long crossbars 40 is attached. The second long crossbar 42 serves to stabilize the two legs 32 to which the long crossbars 42 is attached The long crossbar 40 and the long crossbar 42 each provide a track (not shown). Movably mounted to the track of the long crossbar 40 is a first end of a traverse rod 50. The second end of the traverse rod 50 is movably mounted to the track of the long crossbar 42.

The traverse rod 50 has movably mounted thereon a stimulation coil assembly 60 of the functional electro-magnectic stimulator 20. A lead 62 is attached to the stimulation coil assembly 60. The lead 62 is connected to a microprocessor (not shown) of the functional electro-magnectic stimulator 20.

A first short crossbar 80 is attached to one of the legs 30 and the legs 32. A second short crossbar 82 is attached to a second of the legs 30 and a second of the legs 32. The first short crossbar 80 and the second short crossbar 82 are generally parallel.

The short crossbar 80 and the short crossbar 82 serve to stabilize the two legs 30 to which the two short crossbars 80 are connected. The short crossbar 80 also provides a stopping mechanism for the traverse rod 50. The short crossbar 82 also provides a stopping mechanism for the traverse rod 50.

Figure 2:
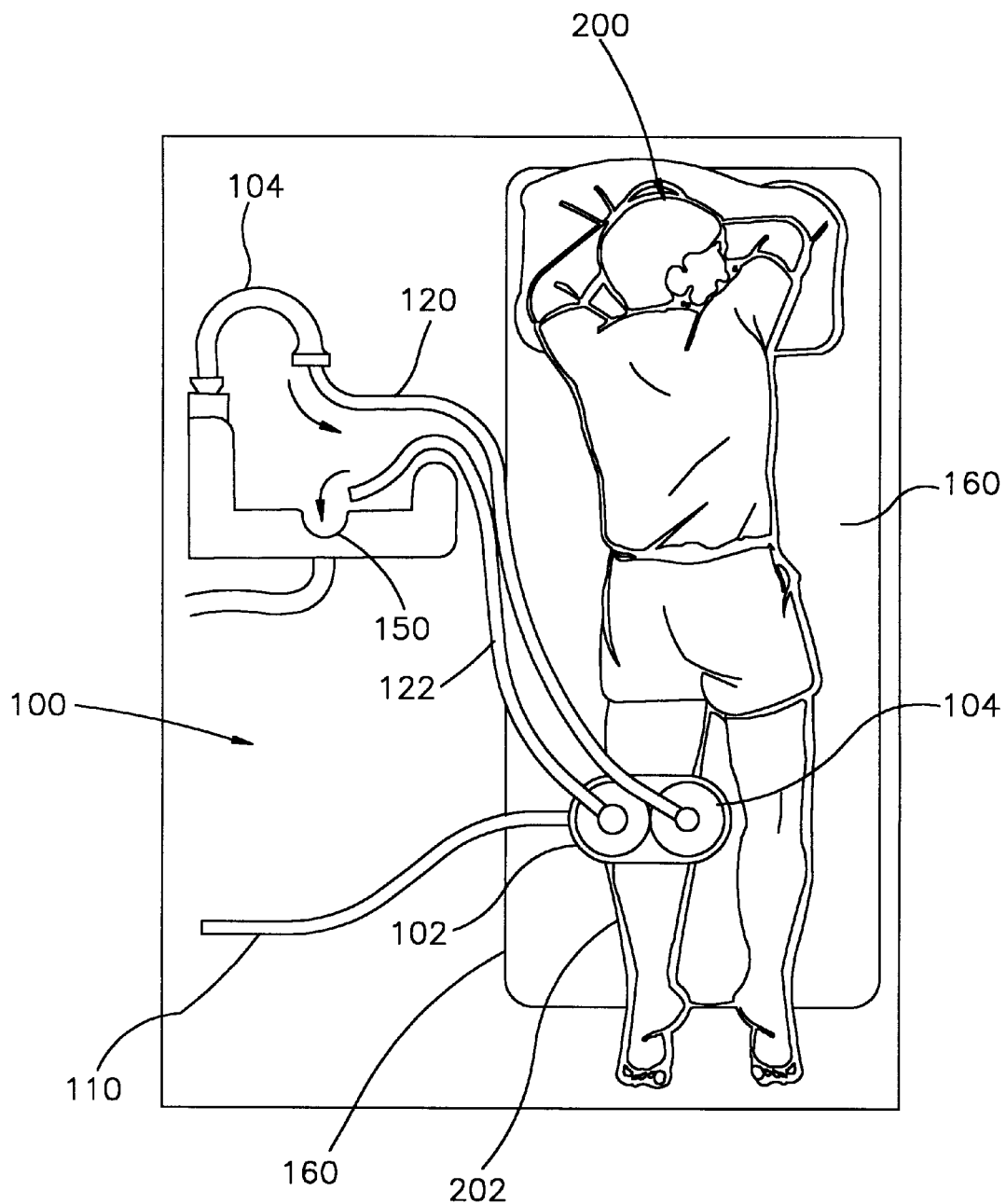
FIG. 2 shows a human subject being treated with electro-magnectic induction according to the present invention.

In FIG. 2 an alternate embodiment of the invention is shown. A functional electro-magnectic stimulator 100 has two coils 102 and 104. Connected with the two coils 102 and 104 is a lead 110. The lead 110 is connected to a microprocessor (not shown).

One end of a hose 120 is connected with a source of cooling fluid (water) from a tap 124. The opposite end of the hose 102 is connected with the functional electro-magnectic stimulator 100. Chambers (not shown) within the functional electro-magnectic stimulator 100 are designed to receive the cooling fluid when the functional electro-magnectic stimulator 100 is operating. A second hose 122 is connected with the functional electro-magnectic stimulator 100. The second hose 122, when the functional electro-magnectic stimulator 100 is operating, receives spent cooling fluid from the functional electro-magnectic stimulator 100. The opposite end of the second hose 122 is positioned with a drain, for, when the functional electro-magnectic stimulator 100 is operating, to deliver the spent cooling fluid to a drain 150.

A bed 160 of suitable size is positioned in close proximity to the functional electro-magnectic stimulator 100. The bed 160 is also in close proximity to the tap 104 and the drain 150.

In use a human subject (not shown) is in the prone position on the upper flat surface 14 of the platform 12 (FIG. 1). The microprocessor (not shown) of the functional electro-magnectic stimulator 20 is programmed and activated. A first command from the microprocessor is transmitted via the lead 62 to cause the traverse rod 50 to traverse the track of the long crossbar 40 and the track of the long crossbar 42 to a point lengthwise on the human subject which is in need of functional magnetic stimulation.

A second command from the microprocessor is transmitted via the lead 62 to cause the causes the stimulation coil assembly 60 of the functional electro-magnectic stimulator 20 to be positioned widthwise on the human subject which is in need of functional magnetic stimulation. A third command from the microprocessor is transmitted via the lead 62 to the functional electro-magnectic stimulator 20 to cause sufficient functional magnetic stimulation for a desired period of time to the human subject.

The apparatus of FIG. 1 can be employed to deliver various treatments to a subject. For instance, the same apparatus of FIG. 1, may be employed for Functional Magnetic Micturition or for the inducement of the cough function.

In a second embodiment per FIG. 2, the functional electro-magnectic stimulator, the stimulation coils 102 and 104 are placed directly on a leg 202 of a human subject 200. The human subject is in the prone position on the bed 160. The hose 120 is connected with a source of cooling fluid (water) from a tap 104 and flow of the cooling fluid begins. The cooling fluid enters the hose 102 which communicates with the chambers (not shown) within the functional electro-magnectic stimulator 100 to cool the coils 102 and 104. The cooling fluid exits the chamber and enters the second hose 122. The cooling fluid exits the hose 122 and enters drain 150.

The two coils 102 and 104 of functional electro-magnectic stimulator 100 are activated by the lead 110 as in the first embodiment. The human subject 200 receives the functional electro-magnectic stimulation as in the first embodiment.

The general parameters for treating a human subject are to expose the human subject to a frequency between 1 Hertz and 150 Hertz, preferably 3 Hertz to 100 Hertz and more preferably 10 Hertz to 40 Hertz. The duration of the electro-magnectic induction stimulation provided is typically for 0.25 to 30 seconds, often 0.5 to 15 seconds, or 0.75 to 8 seconds.

To approximate normal fibrinolytic function, the electro-magnectic induction may be employed in repeated intervals. The intervals may conveniently correspond to 2 to 100 electro-magnectic inductions per minute, typically 2 to 50 per minute, and often 6 to 25 per minute.

The location of the electro-magnectic induction is such that the coil will be placed directly upon the subject, up to a distance of preferably not more than 0.5 meter, more preferably less than 10 cm or 1.0 cm from the surface of the subject. As there is a linear effect to the electro-magnectic radiation, it is desired that the coil be placed relatively close to the subject to accomplish several purposes.

First, by placing the coil close to the subject there will be little over-spray of the electro-magnectic radiation with the avoidance of stimulating other functions, such as the cardiac function. Secondly, by placing the coil relatively close to the subject, the differences in signal strength of the electro-magnectic radiation will be minimized and the output of the stimulator may be maintained at a lower intensity.

Conveniently, the human subject is exposed to a field strength maximum magnetic flux of from 0.5 to 10.0 Tesla.

Preferably, the field strength maximum flux of the electromagnectic induction is from, 0.5 to 10.0 Tesla, conveniently 0.75 to 5.0 Tesla. The electro-magnectic induction device is typically operated between 50% and 100% of the maximum power or about 150 to 500 joules, preferably about 200 to 250 joules, conveniently 60% to 80% of the maximum power. The maximum radiation strength per electromagnectic induction is maintained at 0.5 to 50 microcurie per electro-magnetic induction, preferably 1 to 10 microcurie per electro-magnetic induction.

The following is an exemplification of the present invention:

EXAMPLE I

A human subject fasts for ten hours prior to the start of the test at 9 a.m. and abstain from taking caffeinated drinks, smoking, and exercise in the morning. The subject is placed in the prone position, with a water-cooled butterfly magnetic coil placed on the popliteal region, alternating from side to side every 30 seconds. The magnetic stimulation was administered using a Cadwell MES-10, High-Speed Magnetic Stimulator. The Cadwell MES-10, High-Speed Magnetic Stimulator is capable of generating a maximum field strength, at the center of the coil, of 2.2 Tesla at a frequency of 60 Hz.

The stimulator is controlled by an IBM PC with an interactive program which allowed the stimulator to generate a specific frequency and length of stimulation. The frequency of stimulation, burst length, and inter-burst interval are 30 Hz, 4 seconds, and 26 seconds, respectively. The stimulation intensity is gradually increased from 40% either to a level that produced significant calf muscle contraction or to the subjects comfort level. The session duration was 60 minutes.

Blood samples are collected from the veins of the upper limbs immediately prior (baseline), 10, and 60 minutes post-stimulation. During the 60 minute post-stimulation period, the subject did not do any strenuous activity, but is allowed to walk short distances.

Laboratory tests on the baseline blood samples include erythrocyte sedimentation rate (ESR), leukocyte count, hemoglobin, platelet count, lipid profile (HDL and LDL), activated partial thromboplastin time (APTT), prothrombin time (PT), fibrinogen concentration, and D-Dimer levels. Baseline blood samples and the two post-stimulation samples are tested for fibrinolytic activity.

The dilute whole blood clot lysis time is determined by a modified semi-automatic method using a Sonoclot® Surgical analyzer II. Blood was collected in Hemagard blue top tubes in 3.8% sodium citrate with a blood to citrate ratio of 9:1. The blood was immediately diluted 1:10 into phosphate buffer (pH 7.4) in a glass test tube. Diluted blood was recalcified and bovine thrombin was added. The sample was transferred to plastic cuvettes, and incubated on an ice block for 30 minutes. The cuvettes were then transferred to the Sonoclot® Surgical Analyzer and a specially designed probe was inserted for the analysis of fibrinolysis activity. As the clot lysed, the decreasing viscosity against time was recorded as a curve from which the lysis time was calculated. The reference range of the clot lysis time in 50 healthy volunteers (18 to 70 years old) was from 8 to 24 hours with a mean of 16 hours. All tests were conducted before noon to minimize the diurnal variation in fibrinolytic activity.

The fibrinolytic activity measurements, fibrinolysis onset time and whole blood clot lysis time, were examined at baseline, 10 minutes and 60 minutes post-Functional Magnetic Stimulation, for significant effects of the Functional Magnetic Stimulation protocol. One-way ANOVA's revealed significant effects of the magnetic stimulation on both whole blood clot lysis time (p=0.0001) and onset of lysis time (p=0.0188). Whole blood clot lysis time values decrease from 17.6±1.2 hours at baseline to 13.3±1.1 hours and 12.8±1.1 hours at 10 minutes and 60 minutes post-Functional Magnetic Stimulation, respectively (FIG. 2). The post-stimulation values, 10 minutes and 60 minutes, are significantly different, p=0.0002 and p=0.0014, respectively, from the pre-stimulation whole blood clot lysis time measure, but are not significantly different from each other (p=0.3192). The mean onset of lysis time decreases from a baseline value of 5.4±0.6 hours to 4.1±0.3 hours at 10 minutes post-Functional Magnetic Stimulation and 4.0±0.4 hours at 60 minutes post-Functional Magnetic Stimulation. Both post-Functional Magnetic Stimulation values, 10 minutes and 60 minutes, were significantly different from pre-Functional Magnetic Stimulation values, p=0.0106 and p=0.0167, respectively. The post-Functional Magnetic Stimulation values were not significantly different from each other (p=0.3764).

This experiment demonstrates that Functional Magnetic Stimulation of the leg muscles is effective in enhancing systemic fibrinolysis ex vivo. The clot lysis time decreased from a baseline value of 17.6±1.2 hours to 13.3±1.1 hours at 10 minute post-Functional Magnetic Stimulation, and further decreased to 12.8±1.1 hours at 60-minutes post-Functional Magnetic Stimulation. The results herein demonstrate that Functional Magnetic Stimulation produces an improvement in fibrinolytic activity that occurred quickly and was also observed at 60 minutes post-Functional Magnetic Stimulation.

A significant decrease is observed in the mean whole blood clot lysis time following Functional Magnetic Stimulation. The whole blood clot lysis time is observed to decrease from 17.6±1.3 hours before Functional Magnetic Stimulation to 13.3±1.1 and 12.9±1.1 hours at 10 and 60 minutes post-Functional Magnetic Stimulation respectively.

Therefore, Functional Magnetic Stimulation appears to produce a sustained enhancement of fibrinolysis. This marked, sustained improvement in fibrinolysis may be useful in the prevention of deep vein thrombosis through the daily application of Functional Magnetic Stimulation to the legs for the purpose of dissolving clots that may form between stimulation sessions.

The Functional Magnetic Stimulation-induced muscle contractions of the leg muscles enhanced systemic fibrinolysis ex vivo. The improvement in fibrinolysis occurred immediately following Functional Magnetic Stimulation and was also observed at 60 minutes post-Functional Magnetic Stimulation; therefore, appears to produce a sustained enhancement of systemic fibrinolysis which may prove to be useful in deep vein thrombosis prophylaxis. The time of fibrinolytic onset and dilute whole blood clot lysis time are used as global tests of fibrinolytic activity.

The striking enhancement of fibrinolysis by Functional Magnetic Stimulation is attributed to the massive simultaneous tetanic contractions of the leg muscles generated by Functional Magnetic Stimulation. As described, the subject is stimulated in the prone position with the magnetic coil placed above the popliteal region; therefore, the induced current generated by the changing magnetic field stimulates the major nerves underneath the magnetic coil, specifically the common peroneal and the tibial nerves. The foregoing results in the contraction of muscles in all three compartments of the leg, namely the anterior, lateral, and posterior compartments. Fibrinolytic enhancement is quick and sustained for at least 60 minutes after cessation of the Functional Magnetic Stimulation protocol.

From the above description of the invention, those skilled in the art will perceive improvements, changes and modifications. Such improvements, changes and modifications within the skill of the art are intended to be covered by the appended claims.

What is claimed is:

1. A method of treating a human subject with the following apparatus:

a platform having a length and width, said platform length and width of sufficient dimensions to accommodate an adult human subject, said platform comprising a first surface upon which a human subject, when said apparatus is in use, lies, at least one traversing means connected with said platform, said traversing means having mounted thereon an electro-magnetic induction coil, said electro-magnetic induction coil being movable along at least one axis of said traversing means, for when said apparatus is in use, permitting focusing of electro-magnetic induction upon said human subject;

the method comprising the steps of;

exposing the human subject to sufficient electro-magnetic induction for a sufficient period of time to stimulate endogenous fibrinolysis, wherein more than one electro-magnetic induction is employed per single treatment with an interval between the electro-magnetic inductions from 0.5 to 20 seconds, the electro-magnetic induction is employed in cycles of 0.25 to 20 seconds, and the maximum radiation strength per cycle of the electro-magnetic induction is less than about 50 microcurie per electro-magnetic induction.

2. A method for treating a mammalian subject, in need of treatment for thrombosis, including the steps of exposing the mammalian subject to sufficient electro-magnetic induction for a sufficient period of time to stimulate endogenous fibrinolysis.

3. The method of claim 1 wherein the maximum radiation strength per cycle of the electro-magnetic induction is in the range of 1 to 10 microcurie per electro-magnetic induction.

4. The method of claim 2 wherein the focus of the electro-magnetic induction of the subject is the popliteal region.

5. The method of claim 2 wherein the electro-magnetic induction is employed in cycles of 0.25 to 20 seconds.

6. The method of claim 2 wherein more than one electro-magnetic induction is employed per single treatment.

7. The method of claim 2 wherein the total number of the electro-magnetic induction cycles for each stimulation are 2 to 100.

8. The method of claim 2 wherein more than one electro-magnetic induction is employed per single treatment with an interval between the electro-magnetic inductions from 0.5 to 20 seconds.

9. The method of claim 2 wherein more than one electro-magnetic induction is employed per single treatment with an interval between the electro-magnetic inductions from 0.5 to 20 seconds.

10. The method of claim 2 wherein the thrombosis subject to the treatment is venous thrombosis.

11. The method of claim 2 wherein the thrombosis subject to the treatment is arterial thrombosis.

12. A method for treating a mammalian subject, in need of treatment for embolism, including the steps of exposing the mammalian subject to sufficient electro-magnetic induction for a sufficient period of time to stimulate endogenous fibrinolysis.

13. The method of claim 12 wherein the electro-magnetic induction is employed in cycles of 0.25 to 20 seconds.

14. The method of claim 12 wherein the maximum flux is less than 3.0 Tesla.

15. The method of claim 12 wherein the total number of the electro-magnetic induction cycles for each stimulation are typically from 2 to 100.

16. The method of claim 12 wherein the maximum flux is less than 1.5 Tesla.

17. The method of claim 12 wherein more than one electro-magnetic induction is employed per single treatment with an interval between the electro-magnetic inductions from 0.5 to 20 seconds.

18. A method for treating a human subject, in need of treatment for thrombosis and/or embolism, including the steps of exposing the human subject to sufficient electro-magnetic induction for a sufficient period of time to stimulate endogenous fibrinolysis wherein, more than one electro-magnetic induction is employed per single treatment with an interval between the electro-magnetic inductions from 0.5 to 20 seconds, the electro-magnetic induction is employed in cycles of 0.25 to 20 seconds, and the maximum radiation strength per cycle of the electro-magnetic induction is less than about 50 microcurie per electro-magnetic induction.

* * * * *